(12) United States Patent
Levine et al.

(10) Patent No.: US 9,023,833 B2
(45) Date of Patent: May 5, 2015

(54) METHOD FOR TREATING SEPSIS IN PATIENTS WITH ALBUMIN, CHOLESTEROL AND HDL LEVELS ABOVE MINIMUM THRESHOLDS

(71) Applicants: Daniel M. Levine, New York, NY (US);
Thomas S. Parker, Brooklyn, NY (US);
Bruce R. Gordon, New York, NY (US);
Stuart D. Saal, New York, NY (US)

(72) Inventors: Daniel M. Levine, New York, NY (US);
Thomas S. Parker, Brooklyn, NY (US);
Bruce R. Gordon, New York, NY (US);
Stuart D. Saal, New York, NY (US)

(73) Assignee: Sepsicure, LLC, New York, NY (US)

(*) Notice: Subject to any disclaimer, the term of this patent is extended or adjusted under 35 U.S.C. 154(b) by 24 days.

(21) Appl. No.: 13/718,246

(22) Filed: Dec. 18, 2012

(65) Prior Publication Data
US 2014/0171391 A1    Jun. 19, 2014

(51) Int. Cl.
| A61K 31/685 | (2006.01) |
| A61K 31/575 | (2006.01) |
| A61K 31/23 | (2006.01) |
| A61K 9/00 | (2006.01) |
| A61K 9/107 | (2006.01) |

(52) U.S. Cl.
CPC .............. *A61K 31/575* (2013.01); *A61K 31/23* (2013.01); *A61K 31/685* (2013.01); *A61K 9/0019* (2013.01); *A61K 9/1075* (2013.01)

(58) Field of Classification Search
CPC .. A61K 31/685; A61K 9/0019; A61K 9/1075
USPC .......................................................... 514/78
See application file for complete search history.

(56) References Cited

U.S. PATENT DOCUMENTS

| 5,506,218 A | 4/1996 | Parker et al. |
| 5,587,366 A | 12/1996 | Parker et al. |
| 5,614,507 A | 3/1997 | Parker et al. |
| 5,674,855 A * | 10/1997 | Levine et al. ................... 514/78 |
| 6,740,487 B1 * | 5/2004 | Schwartz et al. ............ 435/6.14 |
| 2002/0111295 A1 * | 8/2002 | Yajima et al. ...................... 514/6 |
| 2004/0037781 A1 * | 2/2004 | McCormack, Jr. ............. 424/45 |
| 2007/0049554 A1 | 3/2007 | Levine et al. |

OTHER PUBLICATIONS

Danner et al. (Endotoxemia in Human Septic Shock, Chest 1991; 99: 169-75.*
Dellinger et al. Efficacy and safety of a phospholipid emulsion (GR270773) in Gram-negative severe sepsis: Results of a phase II multicenter, randomized, placebo-controlled, dose-finding clinical trial, Crit Care Med 2009 vol. 37., No. 11.*
Qian et al. Relationship between serum albumin level prognosis in children with sepsis, severe sepsis or septic shock, Zhonghua Er Ke Ka Zhi, Mar. 2012 50 (3): 184-7.*
Chien et al. Low Serum level of high-density lipoprotein cholesterol is a poor prognostic indicator for severe sepsis, Crit Care Med Aug. 2005:33 (8): 1688-93.*
Yamamoto et al., Dis Colon Rectum, 2000;43:1141-1145.*
Vermont et al., Crit Care Med 2005;33(7)1610-1615.*
Lipid Infusion in Dialysis Patients with Endotoxemia (Lipidose) Clinical Trials.gov (2007).
Marshall, et al., "Diagnostic and Prognostic Implications of Endotoxemia in Critical Illness: Results of the Medic Study," J. Infect. Dis., 190:527-534 (2004).
Dellinger, et al., "Efficacy and safety of a phospholipid emulsion (GR270773) in Gram-negative severe sepsis: Results of a phase II multicenter, randomized, placebo-controlled, dose-finding clinical trial," Crit. Care Med., 37(11):2929-2938 (2009).
Dellinger, et al., "Surviving Sepsis Campaign: International guidelines for management of severe sepsis and septic shock: 2008," Crit. Care Med., 36(1):296-327 (2008).

* cited by examiner

*Primary Examiner* — San-Ming Hui
(74) *Attorney, Agent, or Firm* — Abelman, Frayne & Schwab

(57) ABSTRACT

The invention relates to a method for treating sepsis in subjects who exhibit serum albumin levels, and one of total cholesterol or HDL levels, above minimum threshold values. The method involves intravenous administration of an emulsion, which contains a phospholipid, a neutral lipid, and a cholate salt.

16 Claims, No Drawings

METHOD FOR TREATING SEPSIS IN PATIENTS WITH ALBUMIN, CHOLESTEROL AND HDL LEVELS ABOVE MINIMUM THRESHOLDS

FIELD OF THE INVENTION

This invention relates to treatment of patients suffering from sepsis. More particularly, it relates to treating defined, subpopulations of patients who suffer from this condition.

BACKGROUND AND PRIOR ART

It has been estimated that there are more than 18 million cases of sepsis per year, with the mortality rate in severe cases making it the second leading cause of deaths in non-coronary intensive care units. See, e.g., Dellinger, et al., *Crit. Care Med,* 37(11):2929-2938 (2009), incorporated by reference; Dellinger, et al., *Crit. Care Med,* 36(1):296-327 (2008), also incorporated by reference; Marshall, et al., *J Infect. Diseases,* 190:527-534 (2004), also incorporated by reference.

Broadly defined, "sepsis" refers to the presence of a systemic inflammatory response resulting from bacterial infection. In turn, a systemic inflammatory response is defined as the presence of two or more abnormalities in body temperature, heart rate, respiratory rate or blood gas, and an abnormal white blood cell count. "Severe sepsis" results from dysfunction of one or more organs as a result of the response to the above infection, while "septic shock" occurs with the development of cardiovascular instability, including hypotension, also resulting from a response to the above infection. The term "severe septic shock" includes both severe sepsis and septic shock.

When "sepsis" is used herein, all of the above conditions are encompassed thereunder.

Approaches to treating sepsis include, inter alia, administration of intravenous fluids, antibiotics, vasopressors, and steroids. None have been very successful and in the case of steroids, therapeutic approaches are controversial. Notwithstanding these approaches, as Dellinger et al. (2009), supra, reports, mortality remains high, and a large medical need remains unmet.

U.S. Pat. No. 5,674,855 to Levine, et al., the disclosure of which is incorporated by reference describes emulsions of various materials, which showed efficacy in treatment of endotoxemia. In brief, the emulsions contain a phospholipid (phosphatidylcholine), a neutral lipid (triglyceride), and a cholate salt (sodium cholate). Various ranges of the materials in relationship to each other are described. The patent discloses a process for making the emulsion, as well as methods for the intravenous administration thereof. A product based upon these formulations, referred to as "GR270773," was tested for efficacy in dialysis patients with endotoxemia (see www.clinicaltrials.gov, identifier NCT00506454), and in a very widespread trial reported by Dellinger (2009), supra. The dialysis trial showed no efficacy whatsoever, and the clinical trial reported by Dellinger et al., supra concluded that the emulsion did not show efficacy greater than treatment with a placebo.

It has now been found, however, that emulsions of the type described in the '855 patent do in fact have surprising efficacy in a subset of patients, as defined herein. Such a result was not to be expected from the literature which concluded that the emulsions were ineffective.

Details of this invention are set forth in the Detailed Description of Preferred Embodiments which follows.

DETAILED DESCRIPTION OF PREFERRED EMBODIMENTS

The invention relates to a method for treating sepsis, comprising intravenously administering an amount of an emulsion which comprises (i) a phospholipid, (ii) a neutral lipid, and (iii) a cholate salt, to a subject who presents serum albumin ("Alb" hereafter) at a level of at least 1.5 g/dL, and one or both of total cholesterol ("TC" hereafter) of at least 40 mg/dL, and high density lipoprotein ("HDL" hereafter) of at least 20 mg/dL. Subjects who exhibit these levels of biomarkers exhibit sufficient lipoprotein and have sufficient liver function to respond to the emulsion and clear the toxins causing the sepsis.

While not wishing to be bound to any theory, the parameters used were chosen because they serve as markers for functions key to clearance of sepsis-causing toxins. Albumin is produced by the liver, and its concentration in serum is impacted by many factors. For example, low levels of albumin in critical illnesses are thought to be related to reduce hepatic synthesis, increased catabolism, and capillary leakage. Hence albumin levels serve as a way to measure hepatic clearance of phospholipids.

With respect to cholesterol and HDL, study of the therapeutic emulsion showed that it functioned via delivery of phospholipid to HDL and other lipoproteins. Theoretically, then there must be some level of endogenous lipoprotein that is so low that phospholipid from the emulsion, cannot be sufficiently incorporated into those lipoproteins, thus rendering the emulsion ineffective.

Subjects who exhibit sufficient Alb and TC or Alb and HDL to meet the criteria specified above benefit from the administration of emulsions in accordance with the invention, at a much higher level than patients who do not.

The emulsions contain, relative to each other, from about 5% to about 10% by weight of cholate salt, from about 5% to about 10% by weight of neutral lipid, and from about 80% to about 90% by weight of phospholipid. Other ingredients, e.g., carriers or other inert ingredients may be added, but the ratios of the 3 ingredients relative to each other should be as stated. Preferably, the cholate salt is sodium cholate, the neutral lipid is a triglyceride and the phospholipid is phosphatidylcholine. See U.S. Pat. No. 5,674,855, incorporated by reference, supra, for information on various formulations.

The emulsions should be administered to subjects intravenously, in amounts ranging from about 500 mg/kg of body weight to about 1500 mg/kg of body weight, and most preferably, a dose of from about 750 mg/kg of body weight, to about 1000 mg/kg of body weight, is preferred, over a three-day period. Other dosing schedules may also be used.

Such dosages can be achieved via an initial high loading dose followed by a lower maintenance dose. For example, a bolus of 75 mg/kg/hr for 2 hours followed by 10 mg/kg/hr for 70 hours would achieve an 850 mg/kg dose over a 72-hour period.

In the examples which follow, an emulsion was prepared which contained 7.0 wt. % triglyceride, 7.2 wt. % sodium cholate, and 85.8 wt. % phosphatidylcholine. Subjects received an intravenous dose of 850 mg of emulsion per kg of body weight over a 72-hour period.

EXAMPLE 1

It is accepted that a successful medicament for patients suffering from sepsis should reduce overall mortality by at least 5%, and preferably, at least 7% (see "P-E" in Benefit column below). However, to directly equate the number of patients saved with a successful medicament, a Relative Benefit of 15% to 20% is often a better indicator (see "Relative" in Benefit column below).

Analysis was carried out of samples taken from subjects, as reported in Dellinger et al. (2009), supra. This "Dellinger" study is known as the "LIPOS" trial, and "LIPOS" is used hereafter.

Blood samples were assayed for levels of Alb, TC and HDL, using methods well known in the art. Dellinger et al. (2009), did not measure Alb, and failed to obtain measurements of TC and HDL in patients with such values missing from the original LIPOS data.

TABLE 1

Subjects in Total LIPOS Population

| Group | N | Mortality % (Deaths/Total) | | Benefit | |
| | | Placebo (P) | 850 mg/kg of emulsion (E) | P-E | Relative |
|---|---|---|---|---|---|
| LIPOS | 1197 | 26.9% (161/599) | 25.8% (154/598) | 1.1% | 4.2% |
| AlbTC | 988 | 24.5% (120/490) | 22.5% (112/498) | 2.0% | 8.2% |
| AlbHDL | 593 | 24.1% (72/299) | 20.1% (59/294) | 4.0% | 16.7% |

In Table 1, supra, LIPOS refers to the subjects who were studied in the trial reported in Dellinger et al. (2009). "AlbTC" refers to a subpopulation, where, as noted supra, Alb≥1.5 g/dL and TC≥40 mg/dL. "AlbHDL" represents a group with Alb levels as described, supra, and HDL≥20 mg/dL.

With respect to "Benefit," "P-E" is the mortality reduction, the difference in survival between those who received the emulsion and those who received placebo. The "Relative Benefit" is 1-RR, where RR, the relative risk, is the ratio of the probability of death occurring in the emulsion group versus the placebo group.

Although the Relative Benefit was only 4.2% for the entire LIPOS population, it was 8.2% and 16.7% respectively in the AlbTC and AlbHDL groups, clearly within the desired range.

EXAMPLE 2

Further analysis viewed a subpopulation of LIPOS subjects that did not receive the vasopressor cortisol intravenously, in order to determine how they would respond to the AlbTC and AlbHDL criteria.

Table 2 shows how the AlbTC and AlbHDL criteria select responsive subjects among those that did not receive cortisol. Applying the AlbTC or Alb HDL criteria to this subgroup gives a P-E benefit of 6.2% and 10.8%, respectively, compared to 4.8% without applying the criteria.

TABLE 2

Subgroup: Subjects that did not receive Intravenous Cortisol

| Group | N | Mortality % (Deaths/Total) | | Benefit | |
| | | Placebo (P) | 850 mg/kg of emulsion (E) | P-E | Relative |
|---|---|---|---|---|---|
| LIPOS | 928 | 27.0% (124/459) | 22.2% (104/469) | 4.8% | 17.9% |
| AlbTC | 796 | 25.5% (100/392) | 19.3% (78/404) | 6.2% | 24.3% |
| AlbHDL | 474 | 27.1% (65/240) | 16.2% (38/234) | 10.8% | 40.0% |

This subpopulation of subjects surpassed the 5% P-E benefit criteria for both AlbTC and AlbHDL, with significant Relative Benefits of 24.3% and 40.0% respectively.

EXAMPLE 3

Another analysis took a subpopulation of LIPOS subjects that did not have an intra-abdominal infection. These subjects had Gram-negative bacteremia, nosocomial pneumonia or pyelonephritis.

Table 3 shows this subgroup obtained by excluding subjects with intra-abdominal infection, and only containing subjects with Gram-negative bacteremia, nosocomial pneumonia or pyelonephritis. Here, the AlbTC and AlbHDL criteria give P-E treatment benefits of 6.2% and 8.9% compared to 4.2% without using these criteria.

TABLE 3

Subgroup: Subjects with Gram-Negative Bacteremia, Nosocomial Pneumonia or Pyelonephritis

| Group | N | Mortality % (Deaths/Total) | | Benefit | |
| | | Placebo (P) | 850 mg/kg of emulsion (E) | P-E | Relative |
|---|---|---|---|---|---|
| LIPOS | 566 | 29.0% (80/276) | 24.8% (72/290) | 4.2% | 14.3% |
| AlbTC | 523 | 28.2% (72/255) | 22.0% (59/268) | 6.2% | 22.0% |
| AlbHDL | 336 | 28.0% (47/168) | 19.0% (32/168) | 8.9% | 31.9% |

This subpopulation of subjects also surpassed the 5% P-E benefit criteria for both AlbTC and AlbHDL, with high Relative Benefits of 22.0% and 31.9% respectively.

The foregoing disclosure sets forth the details of the invention which is a method for treating sepsis in a subject who (i) exhibits a serum albumin level of at least 1.5 g/dL, and (ii) exhibits at least one of a total cholesterol level of at least 40 mg/dL, and high density lipoprotein of at least 20 mg/dL, by intravenously administering an emulsion, which comprises (i) a phospholipid, (ii) a neutral lipid, and (iii) a cholate salt, wherein relative to each other, the phospholipid is present at about 80% to 90% by weight, the neutral lipid is present at about 5% to 10% by weight, and the cholate salt is present at about 5% to 10% by weight, in an amount sufficient to treat said sepsis. Preferably, the emulsion is administered over a three day period, in an amount ranging from about 500 mg/kg to about 1500 mg/kg of body weight, and more preferably from about 750 mg/kg of body weight to about 1000 mg/kg of body weight. Most preferably, the dosage is set at 850 mg/kg of body weight.

The mode of administration can vary, i.e., it may be completely continuous over a given time frame, or can take the form of large, "up front" bolus doses followed by smaller, continuous dosing, as shown supra.

The subjects to be treated by the invention may or may not have received a vasopressor, such as cortisol, and may be subjects who do not exhibit intra-abdominal infections, but exhibit one or more of nosocomial pneumonia, pyelonephritis, or bacteremia. The bacteremia may be caused by Gram-negative and/or Gram-positive bacteria, as may be sepsis in general.

Other features of the invention will be clear to the skilled artisan and need not be reiterated here.

The terms and expression which have been employed are used as terms of description and not of limitation, and there is no intention in the use of such terms and expression of excluding any equivalents of the features shown and described or portions thereof, it being recognized that various modifications are possible within the scope of the invention.

We claim:

1. A method for treating a subject suffering from sepsis comprising:
    (i) screening a subject to determine said subject's levels of serum albumin, total cholesterol and high density lipoprotein, and
    (ii) intravenously administering an emulsion comprising (i) a phospholipid, (ii) a neutral lipid, and (iii) a cholate salt, to a subject having (a) a serum albumin level of at least 1.5 g/dL and (b) one or both of a total cholesterol level of at least 40 mg/dL and a high density lipoprotein level of at least 20 mg/dL in an amount sufficient to alleviate said sepsis, but not to a subject who does not exhibit (a) and at least one of (b).

2. The method of claim 1, wherein said emulsion comprises:
    (i) from about 80% to about 90% by weight phospholipid,
    (ii) from about 5% to about 10% by weight neutral lipid, and
    (iii) from about 5% to about 10% by weight cholate salt.

3. The method of claim 1, wherein said phospholipid is phosphatidylcholine.

4. The method of claim 1, wherein said neutral lipid is a triglyceride.

5. The method of claim 1, wherein said cholate salt is sodium cholate.

6. The method of claim 1, comprising administering said emulsion in an amount ranging from about 500 mg/kg of body weight to about 1500 mg/kg of body weight of said subject.

7. The method of claim 6, comprising administering said emulsion over a 72 hour period.

8. The method of claim 6, comprising administering said emulsion in an amount ranging from about 750 mg/kg of body weight to about 1000 mg/kg of body weight.

9. The method of claim 1, wherein said subject has received or is receiving a vasopressor.

10. The method of claim 1, wherein said subject has not received a vasopressor.

11. The method of claim 1, wherein said sepsis is caused by Gram-negative bacteria.

12. The method of claim 1, wherein said sepsis is caused by Gram-positive bacteria.

13. The method of claim 1, wherein said subject suffers from bacteremia.

14. The method of claim 1, wherein said subject suffers from nosocomial pneumonia.

15. The method of claim 1, wherein said subject suffers from pyelonephritis.

16. The method of claim 1, wherein said subject does not suffer from an intra-abdominal infection.

* * * * *